United States Patent [19]
Mühlbauer

[11] Patent Number: 5,782,633
[45] Date of Patent: Jul. 21, 1998

[54] APPLICATOR FOR A DENTAL COMPOUND

[76] Inventor: Ernst Mühlbauer, Elbgaustrasse 248, 22547 Hamburg, Germany

[21] Appl. No.: 828,554

[22] Filed: Mar. 31, 1997

[30] Foreign Application Priority Data

Apr. 10, 1996 [DE] Germany ............ 296 06 540 U

[51] Int. Cl.$^6$ ............................................ A61C 5/04
[52] U.S. Cl. ........................................ 433/90; 222/326
[58] Field of Search ............... 433/89, 90; 222/326

[56] References Cited

U.S. PATENT DOCUMENTS 3,028,672  4/1962  Zandberg .................. 433/90
3,417,971  12/1968  Blank et al. ............... 433/90
4,264,305  4/1981  Rasmussen et al. ......... 433/90

*Primary Examiner*—John J. Wilson
*Attorney, Agent, or Firm*—Alix, Yale & Ristas, LLP

[57] ABSTRACT

Applicator for a dental compound, whose elongate implement body (1, 2) is or can be connected at the front end (3) to a syringe (4) containing the dental compound and has a ram (5) for advancing a plunger contained in the syringe (4), which plunger can be pushed forward by means of a pusher rod (10) protruding out of the rear end of the implement body (1). To avoid the stick-slip effect, the ram and the pusher rod (10) are each connected to a rack (6, 9), between which racks a gearwheel/pinion pair is arranged, which brings about a gear reduction from the pusher rod to the ram.

8 Claims, 1 Drawing Sheet

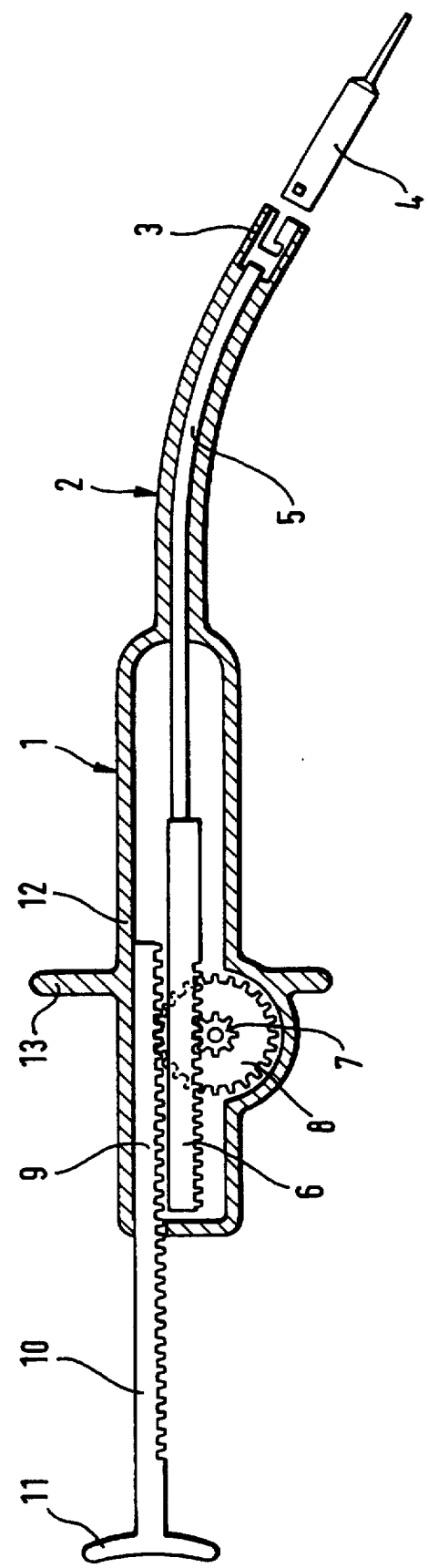

APPLICATOR FOR A DENTAL COMPOUND

FIELD OF THE INVENTION

The invention relates to an applicator for a dental compound, whose elongate body is or can be connected at the front end to a syringe containing the dental compound and has a ram for advancing a plunger contained in the syringe, which plunger can be pushed forward by means of a pusher rod protruding out of the rear end of the implement body.

DESCRIPTION OF THE PRIOR ART

In known applicators of this type (DE-C 25 28 116, DE-A 21 10 465), the ram and the pusher rod are designed to be integral with one another or in any case are firmly connected to one another, so that the movement of the pusher rod is directly transmitted to the ram. The fingers holding the implement remain at a comparatively long distance from the tooth undergoing treatment and are therefore also outside the mouth of the patient. The type of actuation also gives the dentist a very accurate feel for metering the dental compound. Finally, many dentists are also familiar with this type of actuation because these known implements, by virtue of their simplicity, were for a long time the only ones available for metering a dental compound. However, they have the disadvantage that they require high forces, in particular in the case of viscous compounds, and, owing to the changing static friction, do not permit jolt-free emptying. This makes metering difficult.

It is known to provide such implements with a lever mechanism which acts on the pusher rod protruding out of the implement body to the rear and can be actuated like pincers (U.S. Pat. No. 4 198 756). Since these implements are actuated while held in the fist, they have the disadvantage that it is difficult to align them precisely. They also display substantial static friction effects.

An applicator for highly viscous compounds (e.g. epoxy resins) is known from U.S. Pat. No. 5,295,614 for other areas of application (e.g. housing construction), in which applicator a pivotable hand lever acts on a pusher rod via a freewheel coupling and a reducing gear. This implement is also actuated while held in the fist. Although the force transmission of the gear brings about a reduction in the effort required by the user, a number of cycles of the pivot lever is also required to dispense a specific volume from the syringe owing to the gear reduction. When operating it with one hand, aligning such an implement is thus made more complicated, in addition to holding it in the fist, which is already unfavorable, by the required pumping movement of the hand. Since, however, the dentist usually only has one hand free for operation, an applicator of this type is not suitable for use in a dental surgery.

In another group of known implements (U.S. Pat. No. 4, 693,684, U.S. Pat. No. 3,221,409, EP-B 237 182), a lever is arranged at the front end of the implement, which lever can be actuated using the index finger when holding the elongate implement like a pencil, and which acts on the ram by means of a ratchet arrangement or the like. Apart from the fact that these implements are complicated, have a large number of parts and are correspondingly expensive, with these a transverse force is exerted on the ram rod due to the type of actuation, which force causes the friction in the implement body and thus also static friction phenomena. Additionally, these implements have the disadvantage that the actuation must take place near to the point of treatment, and the dentist's hand therefore cannot always remain outside the patient's mouth.

A known implement (U.S. Pat. No. 3 028 672) also belongs to the generic type of implements mentioned above, in which an actuating slide arranged at the front of the implement body is connected to a rack which is connected via a series of gearwheels to the ram which likewise bears a rack. The sense of this gearwheel arrangement consists in the fact that it allows the front part of the implement body containing the ram to be made pivotable relative to the grip part of the implement body, the pivoting axis between the two parts of the implement body coinciding with a gearwheel axis. Since this gearwheel located in the region of the pivoting axis cannot interact directly with the racks of the slide and of the ram for reasons of space, four further transmission gearwheels are required. Speed-transformation is not provided. It is obvious that this arrangement is not only complicated, but also causes increased friction problems.

SUMMARY OF THE INVENTION

The invention sets out from the generic type of applicators mentioned at the beginning and its object is to facilitate the metering.

The pusher rod does not act directly on the ram, as is the case with the prior art of the same generic type, but rather a pair of gearwheels is interposed, which brings about a gear reduction between these two parts, in that the larger gearwheel is connected to the rack of the pusher rod and the smaller pinion is connected to the ram rack. The gear-reducing ratio is determined by the ratio of the diameter of the gearwheel to that of the pinion and is preferably between 2:1 and 5:1, more preferably in the range of 3:1. If a greater gear reduction is required, a plurality of pairs of gearwheels may also be provided.

The advantage of this arrangement consists in the fact that the dentist can assume the posture and operation of the implement familiar to him and nevertheless experiences a speed-transformation which reduces the effort and the friction problems. It is obvious that, for this purpose, the pinion and the gearwheel are connected coaxially to one another securely against rotation and are mounted in the implement body about a fixed axis of rotation.

BRIEF DESCRIPTION OF THE DRAWINGS

The invention is explained in greater detail below with reference to the drawing which depicts an advantageous exemplary embodiment. The single figure shows a longitudinal section through an applicator.

DESCRIPTION OF A PREFERRED EMBODIMENT

The implement body consists of an elongate main part 1 and a front, tapering part 2 which is preferably slightly curved and terminates at the end in a holder 3, in which, for example, the cartridge 4 of a syringe can be inserted and held by means of a bayonet-type attachment arrangement, which cartridge contains the compound to be applied and a plunger. Guided in the front end 2 of the implement body is a flexible ram 5 which can interact in a known manner with the plunger in the cartridge 4 in order to advance the latter. The ram is firmly connected to a ram rack 6 which is guided in its longitudinal direction in the main part 1 of this implement body in a manner not illustrated and interacts with a pinion 7 whose shaft is mounted in the implement body in a manner not illustrated. The pinion 7 is integrally connected to a gearwheel 8 which engages in a rack 9 which merges toward the rear integrally into the pusher rod 10 which bears an actuating plate 11 at the end. The rack 9 or the pusher rod 10 is likewise guided in the main part 1 of the implement body in a suitable manner, for example on one side by its wall 12 and, on the other side, by the circumference of the gearwheel 8 and the opening through which the pusher rod 10 emerges from the implement body at the rear. The two racks 6 and 9 run parallel to one another in the longitudinal direction of the implement body.

The diameters of the gearwheel 8 and the pinion 7 have a ratio to one another of about 3:1. The racks 6, 9 are arranged toward the same side on the gearwheel 8 and pinion 7, so that their movement takes place in each case in the same direction, the movement predetermined by the pusher rod 10 being imparted to the ram, reduced by the gear-reducing ratio.

As can be seen, the implement can be held and used just like known implements in which the pusher rod 10 firmly connected to the ram 5 protrudes out of the rear end of the implement body, namely in that it is gripped with two fingers in front of the abutment 13 and with the thumb on the plate 11. The difference consists in the easier metering facility and - as a result of the gear reduction—lower sensitivity to static friction of the ram in the implement and of the plunger in the cartridge 4.

The mention of a gearwheel/pinion pair in the claim with an indefinite article should not rule out the presence of a possible further gearwheel/pinion pair for even greater gear reduction. The pushing rack 9 then interacts with the gearwheel of the first gearwheel/pinion pair. The pinion of the first gearwheel/pinion pair drives the gearwheel of the second gearwheel/pinion pair, whose pinion acts on the ram rack 6. Whereas in the arrangement of the exemplary embodiment the two racks are arranged on the same side of the gearwheel/pinion pair, in the event of using two gearwheel/pinion pairs, they must be provided on different sides in order to maintain the same direction of movement.

I claim:

1. An applicator for a dental compound comprising:

an elongated implement body having mounting means at the front end thereof for connecting thereto a dental compound syringe containing a plunger;

a pusher rod protruding out of the rear end of said body,
a first rack member connected to the pusher rod;

a ram within said body for advancing the syringe plunger,
a second rack member connected to the ram; and gear reduction means drivably interconnecting said first and second rack members whereby driving movement of said pusher rod and first rack member drivably actuates said second rack member and ram at a reduced speed for controlled actuation of the syringe plunger.

2. The applicator of claim 1 wherein said first and second rack members extend longitudinally along the elongated implement body.

3. The applicator of claim 1 wherein the rack members are positioned generally parallel to each other.

4. The applicator of claim 1 wherein the gear reduction means provides for advancement of the second rack member as the first rack member is advanced.

5. The applicator of claim 1 wherein the gear reduction means includes a gear wheel drivably engageable with said first rack member and a smaller pinion drivably engageable with said second rack member.

6. The applicator of claim 5 wherein the gear wheel and the pinion are coaxially connected.

7. The applicator of claim 1 wherein the gear reduction means provides a gear-reducing ratio within the range of 2:1 to 5:1.

8. The applicator of claim 1 wherein the body provides guide means for guiding the pusher rod and the first rack member.

* * * * *